US00PP30268P2

(12) United States Plant Patent
Eveleens

(10) Patent No.: US PP30,268 P2
(45) Date of Patent: Mar. 5, 2019

(54) ***HYDRANGEA* PLANT NAMED 'HORTMABLO'**

(50) Latin Name: *Hydrangea macrophylla*
Varietal Denomination: Hortmablo

(71) Applicants: KOLSTER HOLDING B.V., Boskoop (NL); HORTEVE BREEDING B.V., Aalsmeer (NL)

(72) Inventor: Cornelis P. Eveleens, Aalsmeer (NL)

(73) Assignees: Kolster Holding B.V., Boskoop (NL); Horteve Breeding B.V., Aalsmeer (NL)

( * ) Notice: Subject to any disclaimer, the term of this patent is extended or adjusted under 35 U.S.C. 154(b) by 0 days.

(21) Appl. No.: 15/731,889

(22) Filed: Aug. 21, 2017

(51) Int. Cl.
*A01H 5/02* (2018.01)

(52) U.S. Cl.
USPC ..... Plt./250
CPC ..... *A01H 5/02* (2013.01)

(58) Field of Classification Search
USPC ..... Plt./250
See application file for complete search history.

(56) References Cited

PUBLICATIONS

UPOV hit on *Hydrangea* plant named 'Hortmablo', QZ PBR 20163225, filed Dec. 20, 2016.*
EU PBR application, Feb. 15, 2017, Horteve Breeding B.V.

* cited by examiner

*Primary Examiner* — Anne Marie Grunberg
(74) *Attorney, Agent, or Firm* — C. A. Whealy

(57) ABSTRACT

A new and distinct cultivar of *Hydrangea* plant named 'Hortmablo', characterized by its upright to broadly spreading plant habit; moderately vigorous to vigorous growth habit and moderate to rapid growth rate; freely branching habit with strong and thick sturdy stems; relatively large leaves; mophead-type inflorescences with large light pink-colored sterile flowers; and good postproduction longevity.

2 Drawing Sheets

Botanical designation: *Hydrangea macrophylla.*
Cultivar denomination: 'HORTMABLO'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'Hortmablo'.

The new *Hydrangea* plant is a product of a planned breeding program conducted by the Inventor in Boskoop, The Netherlands. The objective of the breeding program was to create new *Hydrangea* plants with large inflorescences with numerous and attractive sterile flowers and good postproduction longevity.

The new *Hydrangea* plant originated from a cross-pollination made by the Inventor on Jun. 2, 2010 in Boskoop, The Netherlands, of a proprietary selection of *Hydrangea macrophylla* identified as code number 08-038-06, not patented, as the female, or seed, parent with *Hydrangea macrophylla* 'Snowball', not patented, as the male, or pollen, parent. The new *Hydrangea* plant was discovered and selected by the Inventor as a single flowering plant from within the progeny of the stated cross-pollination in a controlled greenhouse environment in Boskoop, The Netherlands in July, 2014.

Asexual reproduction of the new *Hydrangea* plant by vegetative terminal cuttings in a controlled environment in Boskoop, The Netherlands has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Hortmablo'. These characteristics in combination distinguish 'Hortmablo' as a new and distinct *Hydrangea* plant:

1. Upright to broadly spreading plant habit.
2. Moderately vigorous to vigorous growth habit and moderate to rapid growth rate.
3. Freely branching habit with strong and thick sturdy stems.
4. Relatively large leaves.
5. Mophead-type inflorescences with large light pink-colored sterile flowers.
6. Good postproduction longevity.

Plants of the new *Hydrangea* can be compared to plants of the female parent selection. Plants of the new *Hydrangea* differ primarily from plants of the female parent selection in sterile flower color as sterile flower sepals of plants of the female parent selection are darker in color than sterile flower sepals of plants of the new *Hydrangea*. In addition, plants of the new *Hydrangea* have larger leaves and sterile flower sepals than plants of the female parent selection.

Plants of the new *Hydrangea* can be compared to plants of the male parent, 'Snowball'. Plants of the new *Hydrangea* differ primarily from plants of 'Snowball' in sterile flower color as plants of 'Snowball' have white-colored sterile flower sepals. In addition, inflorescences of plants of the new *Hydrangea* are more flattened than and not as globular as inflorescences of plants of 'Snowball'.

Plants of the new *Hydrangea* can be compared to plants of the *Hydrangea macrophylla* 'Hokomathyst', disclosed in U.S. Plant Pat. No. 22,261. In side-by-side comparisons plants of the new *Hydrangea* differ primarily from plants of 'Hokomathyst' in the following characteristics:

1. Plants of the new *Hydrangea* have larger leaves than plants of 'Hokomathyst'.
2. Plants of the new *Hydrangea* have larger sterile flower sepals than plants of 'Hokomathyst'.
3. Plants of the new *Hydrangea* and 'Hokomathyst' differ in sterile flower color as plants of 'Hokomathyst' have red purple-colored sterile flower sepals with green-colored margins.

Plants of the new *Hydrangea* can also be compared to plants of the *Hydrangea macrophylla* 'Hortmasnodo', not patented. In side-by-side comparisons plants of the new *Hydrangea* differ primarily from plants of 'Hortmasnodo' in sterile flower color as plants of 'Hortmasnodo' have sterile flower sepals that are white in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'Hortmablo'.

The photograph on the second sheet is a close-up view of a typical inflorescence of 'Hortmablo'.

DETAILED BOTANICAL DESCRIPTION

Plants used in the aforementioned photographs and in the following description were grown during the late spring in 17-cm containers in a glass-covered greenhouse in Boskoop, The Netherlands and under cultural practices typical of commercial *Hydrangea* production. During the production of the plants, day temperatures ranged from 18° C. to 25° C. and night temperatures ranged from 16° C. to 17° C. Plants of the new *Hydrangea* were two years old when the photographs and description were taken. Plants of the new *Hydrangea* are not typically treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'Hortmablo'.

Parentage:

*Female, or seed, parent.*—Proprietary selection of *Hydrangea macrophylla* identified as code number 08-038-06, not patented.

*Male, or pollen, parent.*—*Hydrangea macrophylla* 'Snowball', not patented.

Propagation:

*Type cutting.*—By vegetative terminal cuttings.

*Time to initiate roots, summer.*—About three weeks at temperatures about 15° C. to 25° C.

*Time to produce a rooted young plant, summer.*—About six weeks at temperatures about 15° C. to 25° C.

*Root description.*—Medium in thickness, fibrous; typically creamy white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Upright and broadly spreading plant habit; overall plant shape is flattened globular; strong and sturdy lateral branches; moderate to rapid growth rate and moderately vigorous to vigorous growth habit.

*Plant height.*—About 55 cm.

*Plant diameter or area of spread.*—About 68.5 cm.

Lateral branch description:

*Branching habit.*—Freely branching habit; when pinched, about ten lateral branches develop per plant.

*Length.*—About 30.9 cm.

*Diameter.*—About 8 mm.

*Internode length.*—About 9.2 cm.

*Texture.*—Smooth, glabrous; fully developed, woody.

*Aspect.*—Upright to about 30° from vertical.

*Strength.*—Strong, sturdy.

*Color.*—When developing: Close to 144B. Developed: Close to 144A to 144B; at the internodes, tinged with close to N186C; when woody, close to 199C and 200D.

*Lenticels.*—Density: Moderate to dense. Length: About 2.5 mm. Diameter: About 0.5 mm. Color: Close to N186C.

Leaf description:

*Arrangement.*—Opposite, simple.

*Length.*—About 15.3 cm.

*Width.*—About 10.4 cm.

*Shape.*—Broadly elliptic to broadly ovate.

*Apex.*—Apiculate.

*Base.*—Short attenuate.

*Margin.*—Serrate.

*Texture, upper surface.*—Smooth to slightly rugose, glabrous.

*Texture, lower surface.*—Smooth to slightly rugose, surface mostly glabrous, however small tufts of short hairs present at vein axils.

*Venation pattern.*—Pinnate.

*Color.*—Developing leaves, upper surface: Close to 144A. Developing leaves, lower surface: Close to 144B. Fully expanded leaves, upper surface: Close to 137A; venation, close to 145A to 145B. Fully expanded leaves, lower surface: Close to 144A; venation, close to 145B.

*Petioles.*—Length: About 2.8 cm. Diameter: About 5 mm. Texture and luster, upper and lower surfaces: Smooth, glabrous; slightly glossy. Color, upper surface: Close to 145B; towards the margins, close to 144B. Color, lower surface: Close to 145A.

Flower description:

*Flower type and habit.*—Showy sterile flowers and small inconspicuous fertile flowers arranged on mophead-type terminal panicles; panicles globular and slightly flattened in shape; fertile flowers face mostly upright and sterile flowers face upright to outwardly and slightly drooping depending on their position in the inflorescence.

*Fragrance.*—None detected.

*Natural flowering season*.—Plants flower from late spring to late summer in The Netherlands.

*Flower longevity*.—Fertile flowers last about five days on the plant, fertile flowers not persistent; sterile flowers last about six weeks on the plant, sterile flowers persistent.

*Quantity of flowers*.—Freely flowering habit; about 20 fertile flowers per panicle and about 120 sterile flowers per panicle.

*Panicle height*.—About 11.5 cm.

*Panicle diameter*.—About 17.9 cm.

*Fertile flower buds*.—Length: About 4 mm. Diameter: About 4 mm. Shape: Obovate. Color: Close to NN155B; towards the base, close to 145B to 145C.

*Sterile flower buds*.—Length: About 3 mm. Diameter: About 3.5 mm. Shape: Flattened globular. Color: Close to 69B to 69C.

*Fertile flower diameter*.—About 1.2 cm.

*Fertile flower depth* (*height*).—About 9 mm.

*Sterile flower diameter*.—About 5.5 cm.

*Sterile flower depth* (*height*).—About 2.4 cm.

*Petals, fertile flowers*.—Quantity and arrangement: Four or occasionally five in a single whorl. Length: About 6 mm. Width: About 3 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to 155C. When opening and fully opened, lower surface: Close to 155C; towards the base, close to NN155D.

*Petals, sterile flowers*.—Quantity and arrangement: About four or occasionally five in a single whorl. Length: About 4 mm. Width: About 3 mm. Shape: Ovate, concave. Apex: Acute. Base: Cuneate. Margin: Entire. Texture and luster, upper and lower surfaces: Smooth, glabrous; matte. Color: When opening, upper surface: Close to 75D; towards the margins, close to NN155D. When opening, lower surface: Close to NN155A; towards the apex, tinged with close to 75D. Fully opened, upper surface: Close to NN155A; slightly tinged with close to 75D. Fully opened, lower surface: Close to NN155A; towards the apex, slightly tinged with close to 75D.

*Sepals, fertile flowers*.—Quantity and arrangement: Five or occasionally six in a single whorl. Length: About 2 mm. Width: About 1.5 mm. Shape: Ovate. Apex: Acute. Base: Broadly cuneate. Margin: Entire. Texture and luster, upper and lower surfaces: Smooth, glabrous; matte. Color: When opening, upper and lower surfaces: Close to between 150D and 155A. Fully opened, upper and lower surfaces: Close to between 150D and 155A; color does not change with development.

*Sepals, sterile flowers*.—Quantity and arrangement: Four in a single whorl. Length: About 2.8 cm. Width: About 3.9 cm. Shape: Roughly reniform. Apex: Emarginate, praemorse. Base: Cuneate. Margin: Crenate. Texture and luster, upper and lower surfaces: Smooth, glabrous; matte. Color: When opening, upper and lower surfaces: Close to NN155D; distally, tinged with close to 69D. Fully opened, upper surface: Close to 69B; towards the base, close to 65B to 65C; color becoming closer to 145B with development. Fully opened, lower surface: Close to 69B; venation, close to 65B; color becoming closer to 145C with development.

*Pedicels, fertile flowers*.—Length: About 2 mm. Diameter: About 1 mm. Strength: Moderately strong. Aspect: About 20° from vertical. Texture and luster: Moderately to densely pubescent; matte. Color: Close to 65D.

*Pedicels, sterile flowers*.—Length: About 2.2 cm. Diameter: About 2 mm. Strength: Moderately strong. Aspect: About 45° from vertical. Texture and luster: Moderately pubescent; matte. Color: Close to N155B.

*Reproductive organs, fertile flowers*.—Stamens: Quantity per flower: About ten. Filament length: About 5.5 mm. Filament color: Close to NN155D. Anther length: About 1 mm. Anther shape: Oblong. Anther color: Close to 157D. Pollen amount: Moderate. Pollen color: Close to 159D. Pistils: Pistil quantity per flower: About three or four. Pistil length: About 1 mm. Stigma shape: Club-shaped. Stigma color: Close to NN155D. Style length: About 0.5 mm. Style color: Close to NN155B. Ovary color: Close to between 150D and 155A.

*Reproductive organs, sterile flowers*.—Stamens: Quantity per flower: About eight. Filament length: About 2.5 mm. Filament color: Close to NN155C. Anther length: About 1 mm. Anther shape: Oblong. Anther color: Close to 155A. Pollen amount: Moderate. Pollen color: Close to 159D. Pistils: Pistil quantity per flower: About three or four. Pistil length: About 1 mm. Stigma shape: Club-shaped. Stigma color: Close to NN155A. Style length: About 1 mm. Style color: Close to NN155A. Ovary color: Close to 145D.

*Seeds*.—Seed development has not been observed on plants of the new *Hydrangea* to date.

Disease & pest resistance: Under commercial production conditions, plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 to 9.

It is claimed:

1. A new and distinct *Hydrangea* plant named 'Hortmablo' as illustrated and described.

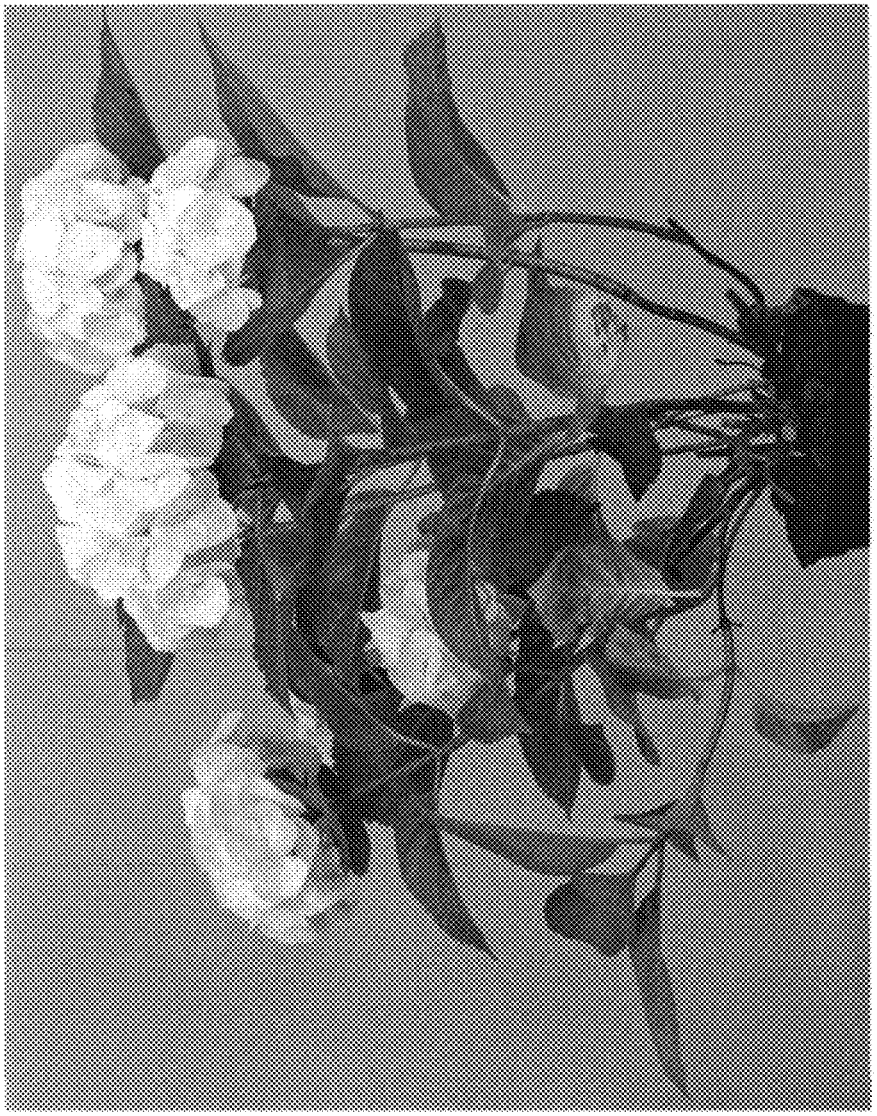

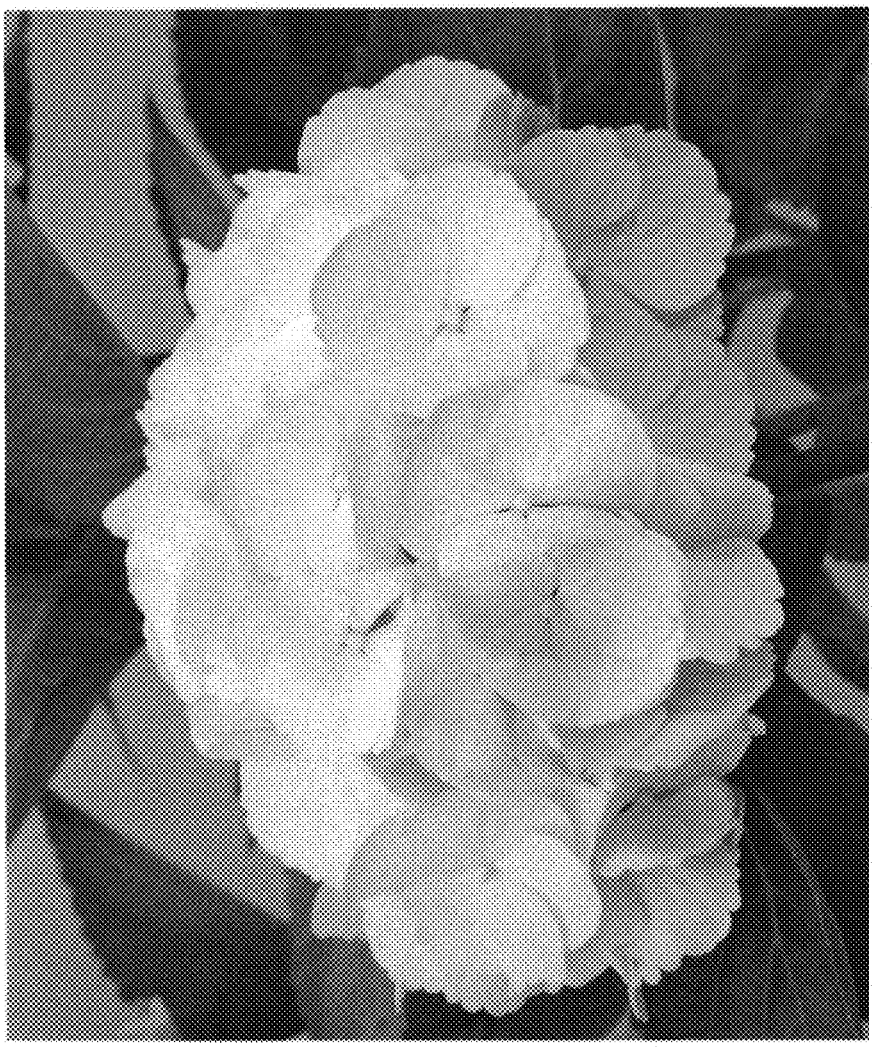

* * * * *